(12) United States Patent
Lozano

(10) Patent No.: US 8,078,275 B2
(45) Date of Patent: Dec. 13, 2011

(54) REGULATION OF NEUROTROPHINS

(75) Inventor: Andres M. Lozano, Toronto (CA)

(73) Assignee: Functional Neuromodulation Inc. (CA)

( * ) Notice: Subject to any disclaimer, the term of this patent is extended or adjusted under 35 U.S.C. 154(b) by 646 days.

(21) Appl. No.: 11/303,619

(22) Filed: Dec. 16, 2005

(65) Prior Publication Data
US 2007/0067002 A1    Mar. 22, 2007

Related U.S. Application Data

(60) Provisional application No. 60/671,723, filed on Apr. 15, 2005.

(51) Int. Cl.
*A61N 1/18* (2006.01)
(52) U.S. Cl. .......................................................... 607/3
(58) Field of Classification Search ................ 607/45, 607/57, 891.1
See application file for complete search history.

(56) References Cited

U.S. PATENT DOCUMENTS

| | | | |
|---|---|---|---|
| 6,356,784 B1 * | 3/2002 | Lozano et al. ................ | 607/2 |
| 6,815,431 B2 | 11/2004 | Tuszynski | |
| 6,885,888 B2 * | 4/2005 | Rezai ............................ | 607/9 |
| 7,598,049 B2 * | 10/2009 | Ray et al. .................. | 435/7.21 |
| 2003/0014089 A1 * | 1/2003 | Chow et al. .................. | 607/54 |
| 2003/0097121 A1 * | 5/2003 | Jolly et al. ................ | 604/891.1 |
| 2005/0033377 A1 * | 2/2005 | Milojevic et al. ............ | 607/45 |
| 2005/0075701 A1 * | 4/2005 | Shafer ......................... | 607/72 |
| 2005/0171579 A1 * | 8/2005 | Tasche et al. ............... | 607/57 |

FOREIGN PATENT DOCUMENTS
WO    WO 03039660 A1 *    5/2003

OTHER PUBLICATIONS

Balkowiec et al. Activity-Dependent Release of Endogenous Brain-Derived Neurotrophic Factor from Primary Sensory Neurons Detected by ELISA In Situ. The Journal of Neuroscience. Oct. 1, 2000, 20(19):7417-7423.*

* cited by examiner

*Primary Examiner* — Carl H Layno
*Assistant Examiner* — Jeremiah Kimball
(74) *Attorney, Agent, or Firm* — Wilson Sonsini Goodrich & Rosati

(57) ABSTRACT

Disclosed are methods for regulating neurotrophin levels within a human body. The invention utilizes an implantable signal generator to deliver stimulation to neural tissue elements. Alternatively, an implantable pump may be utilized to delivery one or more drugs. The implanted device delivers treatment therapy to the neural tissue to thereby alter the level of neurotrophic factors such as BDNF expressed by the influenced neural tissue. A sensor may be used to detect various symptoms of a nervous system disorder. A microprocessor algorithm may then analyze the output from the sensor to regulate the treatment therapy delivered to the body. The invention describes a novel method to regulate the intrinsic levels of neurotrophins and may be used to treat patients with neurological and cognitive disorders.

28 Claims, 5 Drawing Sheets

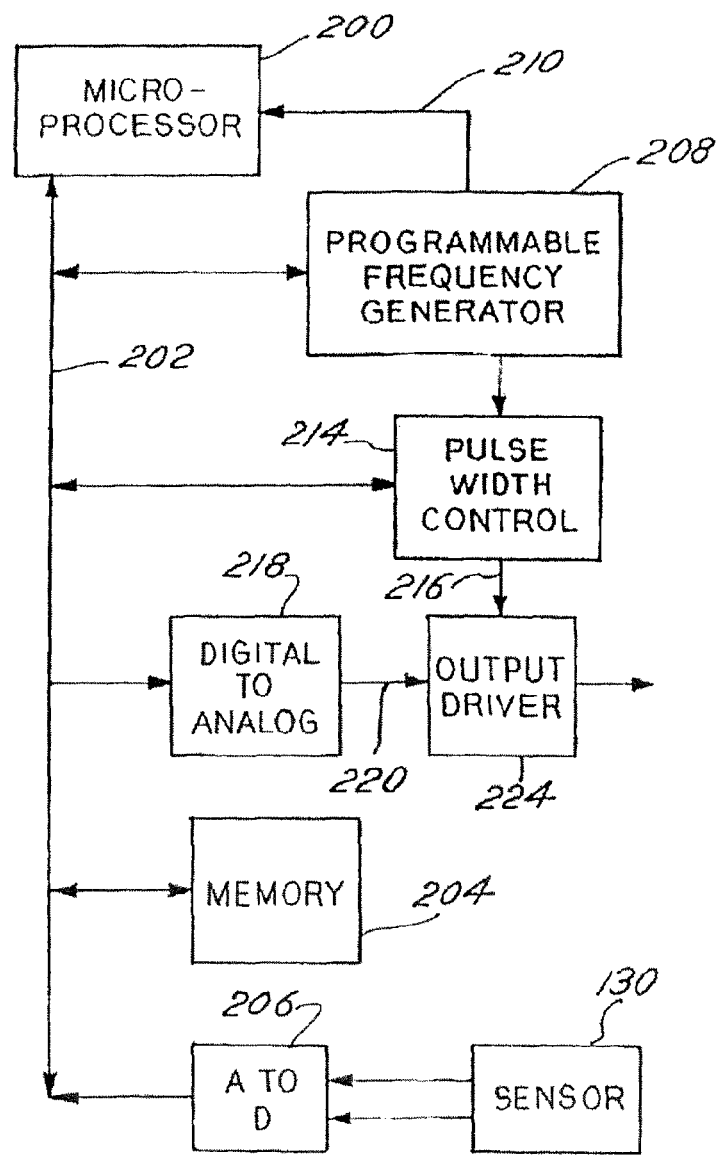

REGULATION OF NEUROTROPHINS

This patent application claims priority to U.S. Provisional Application Ser. No. 60/671,723 filed Apr. 15, 2005, which is incorporated herein by reference in its entirety.

FIELD OF THE INVENTION

The present invention relates to techniques for regulating the level of one or more neurotrophic factors within a human body by way of electrical stimulation and/or drug infusion.

BACKGROUND OF THE INVENTION

It has generally been believed that loss of neurons in the adult human brain—as it occurs in aging humans and in neurological disorders—is an irreversible process. Many major diseases of the human brain involve deficiencies of select neuronal populations. The inability by the adult human brain to generate replacement cells is thought to be a leading cause for the irreversible and progressive nature of several neurological diseases and is responsible for persistent and ongoing impairment. In most regions of the human brain, the generation of neurons is generally confined to a discrete developmental period. After this developmental period, it believed that further generation of brain cells occurs only to a limited extent and is restricted to specific areas in the living human brain.

Neurotrophins play an important role in the development, regeneration, synaptogenesis and connectivity of neurons in mammals. Neurons—such as basal forebrain cholinergic neurons, motor neurons and sensory neurons of the central nervous system—remain responsive to neurotrophic factors even in adult humans. The presence of neurotrophic factors may even facilitate the regeneration of neurons and the repair of neural circuits after loss or damage. Work with cell cultures and animal models has shown that neurotrophins prevent neuronal death, induce neural sprouting and enhance neural recovery and repair. In addition to neurogenesis, neurotrophins are known to have a variety of beneficial effects on neurons including, neuroprotection, rescue from toxicity or injury, and induction of synaptogenesis.

Moreover, while no evidence yet exists that a lack of neurotrophins underlies the etiology of any neurodegenerative disease, these studies have spurred on hopes that neurotrophins might be useful symptomatic-therapeutic agents. It is believed that neurotrophins may be useful for the treatment of neurodegenerative conditions such as Alzheimer's Disease (AD), Parkinson's Disease (PD), amyotrophic lateral sclerosis (ALS), peripheral sensory neuropathies and spinal cord injuries. In addition, neurotrophins may act on neurons affected by other neurological and psychiatric pathologies including ischemia, epilepsy, depression and eating disorders. For example, Brain-Derived Neurotrophic Factor (BDNF) is known to modulate synaptic function as well as to promote neuronal growth in the adult brain. The reduction in BDNF expression for example has been implicated to be important in stress and in depression.

In the prior art, attempts have been made to treat neurodegenerative conditions by infusing neurotrophins into to the patient. For example, U.S. Pat. No. 6,815,431 discloses methods for intraparenchymal delivery of neurotrophins to defective, diseased or damaged cells in the mammalian brain using a lentiviral expression vector. However, the prior fails to disclose any techniques for regulating the human body's own expression of neurotrophic factors.

BRIEF SUMMARY OF THE INVENTION

An embodiment of the invention uses electrical stimulation of nerve elements of a human body to regulate the expression of neurotrophic factors. The treatment is carried out by an implantable signal generator and at least one implantable electrode having a proximal end coupled to the signal generator and having a stimulation portion for electrically affecting nerve elements of the human body. In one embodiment, the method regulates the expression of Brain-Derived Neurotrophic Factor (BDNF) in the brain to treat various neurodegenerative, neurological, psychiatric and cognitive disorders. Alternatively, the treatment may be carried out by an implantable pump and at least one catheter having a proximal end coupled to the pump and having a discharge portion for infusing therapeutic dosages of the one or more drugs into a predetermined infusion site at or near nerve elements. By using the foregoing techniques, the nerve elements may be stimulated to increase or decrease its production of neurotrophic factors. In other embodiments of the invention, drug infusion may be used as treatment therapy instead of or in addition to the electrical stimulation.

In another embodiment of the invention, a sensor is used in combination with the signal generator and stimulating electrodes to regulate expression of neurotrphic factors. Control means responsive to the sensor may thereby regulate the signal generator and/or pump so that the neurological disorder is treated.

By using the foregoing techniques, neurodegenerative and cognitive disorders can be controlled or treated through the regulation of the expression of neurotrophic factors.

BRIEF DESCRIPTION OF THE DRAWINGS

FIG. 3 is a schematic block diagram of a microprocessor and related circuitry of an implantable medical device for use with the invention.

DETAILED DESCRIPTION OF THE INVENTION

The invention discloses techniques for delivering treatment therapy to nerve elements of a human body to regulate the body's expression of neurotrophic factors. In an embodiment, the regulation of Brain-Derived Neurotrophic Factor (BDNF) in the brain may be performed to treat various neurodegenerative, neurological, psychiatric and cognitive disorders and/or to treat locations of the body exhibiting neuronal loss or damage. However, it will be appreciated by those skilled in the art that the present application covers regulation of any number of neurotrophic factors and their receptors including, but not limited to, Artemin, CNTF, Erbs, EGF, FGFs, GDNF, GFRas, gp130, IGFs, Neuregulins, Neurturin, b-NGF, NT-3, NT-4, Neuropilins, PDGFs, Persephin, Ret, Trks, and VEGFs.

Moreover, depending on where it is desired to regulate neurotrophin expression, any nerve area of the human body may be influenced including the brain (cortical areas and sub-cortical areas such as deep brain elements), the spinal cord or peripheral nerves. Accordingly, the invention incorporates electrical stimulation and/or drug infusion techniques to directly or indirectly influence tissue elements within the brain. One or more electrodes and/or catheters are implanted in the brain so that the stimulation or infusion portions lie within or in communication with predetermined portions of the brain. The electrical stimulation or drug therapy influences the predetermined brain elements to achieve the desired result in the expression of neurotrophic factors.

These techniques of the present invention are suitable for use within any implantable medical device. In a preferred embodiment, the present invention is implemented within an implantable neurostimulator system, however, those skilled in the art will appreciate that the present invention may be implemented generally within any implantable medical device system including, but not limited to, implantable drug delivery systems, implantable systems providing stimulation and drug delivery.

The present invention may be utilized to treat, for example, any number of conditions that result from neuronal loss or damage including, but not limited to, depression, epilepsy, post cranial irradiation, steroid induced impairment, stress disorders, cognitive disorders, Alzheimer's disease, and other neurodegenerative diseases. Such other neurodegenerative diseases include, for example, Amyotrophic lateral sclerosis (ALS), Huntingtons, Spinocerebellar ataxias (SCA's). Moreover, in certain applications, the present application may be desirable to reduce the level of neurotrophins in a body. For example, circumstances where it may desirable to reduce levels of neurotrophins include in cases of painful neuropathies to reduce neural sprouting and in cases of epilepsy to reduce maladaptive sprouting and synaptogenesis.

Figure 4A:
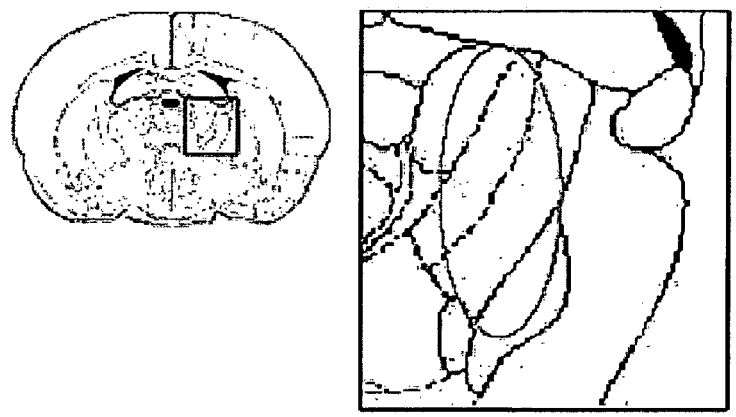
FIG. 4(a) is a diagram depicting the anterior thalamic nuclei complex and FIG. 4(b) is a diagram depicting the dentate gyrus.
Figure 4B:
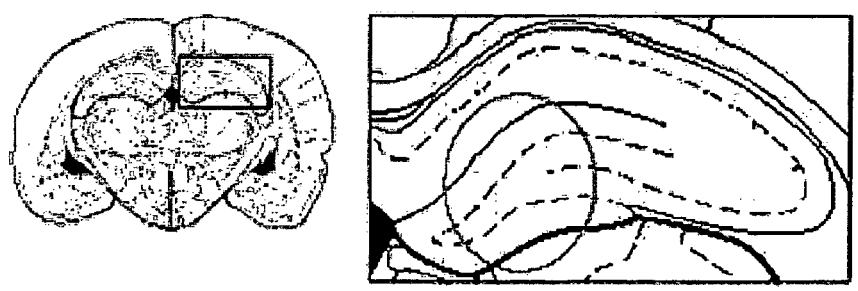

As discussed, the targeted treatment site includes any nerve location within the body, and in one embodiment includes the brain (the cortex and/or the sub-cortex). For cortex stimulation, a multi contact cortical brain surface electrode (e.g., Medtronic Resume) may be utilized. For sub-cortex stimulation, a deep brain electrode may be utilized. The sub-cortex can include deep brain elements such as, for example, the anterior thalamic nuclei complex (FIG. 4(a)), the dentate gyrus (FIG. 4(b)), the periventricular zone, the Papez circuit, and the cerebellum. The Papez circuit is generally a neuronal circuit in the limbic system, consisting of the hippocampus, formix, mammillary body, anterior thalamic nuclei, and cingulate gyrus. Stimulation or drug therapy along the Papez circuit may lead to expression of neurotrophic factors in the hippocampus. When the periventricular zone is influenced in accordance with the present invention, new neurons may migrate to the striatum, cortex, or the substantia nigra, and brainstem and therefore lead to expression of neurotrophic factors in such areas. The cerebellum is another brain location where increased expression of neurotrophic factors may be therapeutically desirable. In general, the foregoing techniques may be used to regulate expression of neurotrophic factors by application of electrical stimulation or drug therapy in either the cerebellum or cerebellar afferent or efferents.

Thus, the site of stimulation or drug infusion may be chosen based on the neural structures that are affected by neuronal loss and which ones would benefit from the regulation of neurotrophincs. For example, targeting the hippocampal neuronal loss may utilized to treat depression, epilepsy, post cranial irradiation, steroid induced impairment in neurogenesis, stress disorders, cognitive disorders and Alzheimer's disease. Targeting the cortical, striatal, substantia nigra, brainstem and cerebellar loss may be utilized to treat Huntington's Disease, Alzheimers, multiple system atrophy, Parkinson's disease, post-irradiation disorders, paraneoplastic disorders and the Spinocerebellar ataxias. The techniques of the present invention may also be applicable to treat neuronal loss that occurs as a consequence of congenital disorders, stroke, anoxia, hypoxia, hypoglycemia, metabolic disorders, head injury, drug and alcohol toxicity, nutritional deficiencies, auto-immune disorders, immune disorders, infectious and inflammatory processes.

Figure 1:
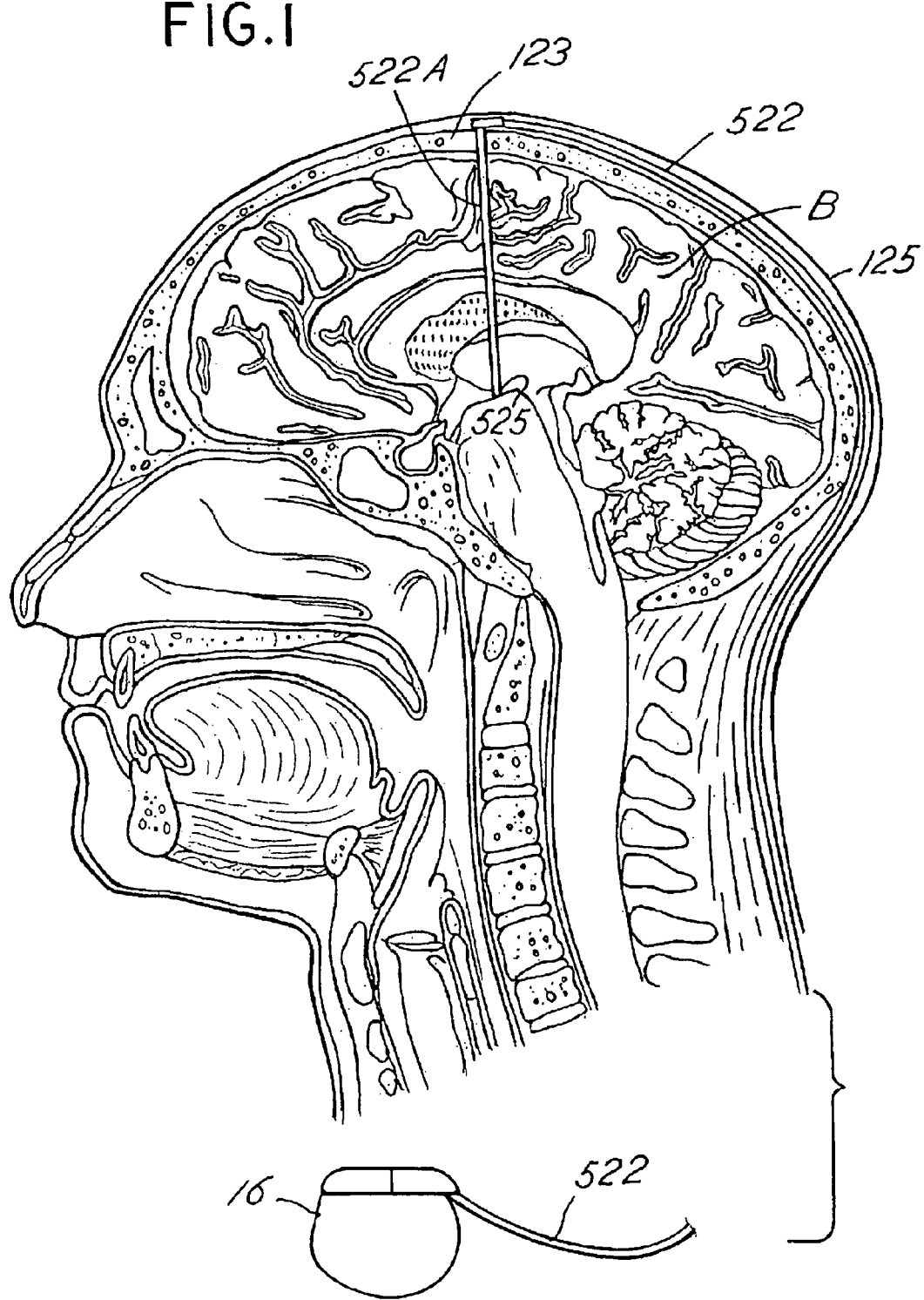
FIG. 1 is a diagrammatic illustration of an electrode implanted in a brain according to a preferred embodiment and a signal generator coupled to the electrode.

Referring to FIG. 1, an implantable neurostimulator device 16 made in accordance with the preferred embodiment may be implanted below the skin of a patient. A lead 522A is positioned to stimulate a specific site 525 in a brain (B). Device 16 may take the form of a modified signal generator Model 7424 manufactured by Medtronic, Inc. under the trademark Itrel II which is incorporated by reference. Lead 522A may take the form of any of the leads sold with the Model 7424 such as Model 3387, for stimulating the brain, and is coupled to device 16 by a conventional conductor 522. One or more external programmers (not shown) may be utilized to program and/or communicate bi-directionally with the implanted device 16.

As shown, the distal end of lead 522A terminates in four stimulation electrodes implanted into a portion of the brain by conventional stereotactic surgical techniques. Each of the four electrodes is individually connected to device 16 through lead 522A and conductor 522. Lead 522A is surgically implanted through a hole in the skull 123 and conductor 522 is implanted between the skull and the scalp 125 as shown in FIG. 1. Conductor 522 is joined to implanted device 16 in the manner shown. Referring to FIG. 2A, device 16 is implanted in a human body 120 in the location shown. Body 120 includes arms 122 and 123. Alternatively, device 16 may be implanted in the abdomen. Conductor 522 may be divided into twin leads 522A and 522B that are implanted into the brain bilaterally as shown. Alternatively, lead 522B may be supplied with stimulating pulses from a separate conductor and signal generator. Leads 522A and 522B could be 1) two electrodes in two separate nuclei that potentiate each others effects or 2) nuclei with opposite effects with the stimulation being used to fine tune the response through opposing forces. It will be appreciated, however, that any number of electrodes may be implanted within the brain in accordance with the invention. Additionally, one or more secondary electrodes may be implanted so that a secondary stimulation portion lies in communication with another predetermined portion of a brain. Moreover, as will be discussed below, one or more catheters, coupled to a pump, may be implanted so that a secondary stimulation portion lies in communication with the tissue elements of the brain.

The device 16 may be operated to deliver stimulation to deep brain tissue elements to thereby regulate expression of neurotrophic factors within the human brain. The particular stimulation delivered may be performed by selecting amplitude, width and frequency of stimulation by the electrode. The possible stimulations include between 2 Hertz and 1000 Hertz for frequency, between 0.1 Volts and 10.0 Volts for pulse amplitude, and between 30 μSeconds and 450 μSeconds for pulse width. The system may be utilized in monopolar, bipolar, or multipolar configurations, in an either continuous or cyclical mode, and in either an open loop or closed loop mode. In one embodiment, the applicant of the present application has shown through experimentation that Deep Brain Stimulation (DBS) in a rodent model increased the expression of BDNF. The applicant used a Western Blot where the levels of BDNF protein were measured (using a BDNF specific antibody) in the hippocampus of a rat receiving DBS in the anterior thalamus. Stimulation at high frequency using the above parameters caused a large increase in the levels of BDNF protein. This increase was specific to BDNF because the level of other proteins, such as the intracellular general metabolic protein glyceraldehyde phosphate dehydrogenase, was unaffected by DBS.

Figure 2:
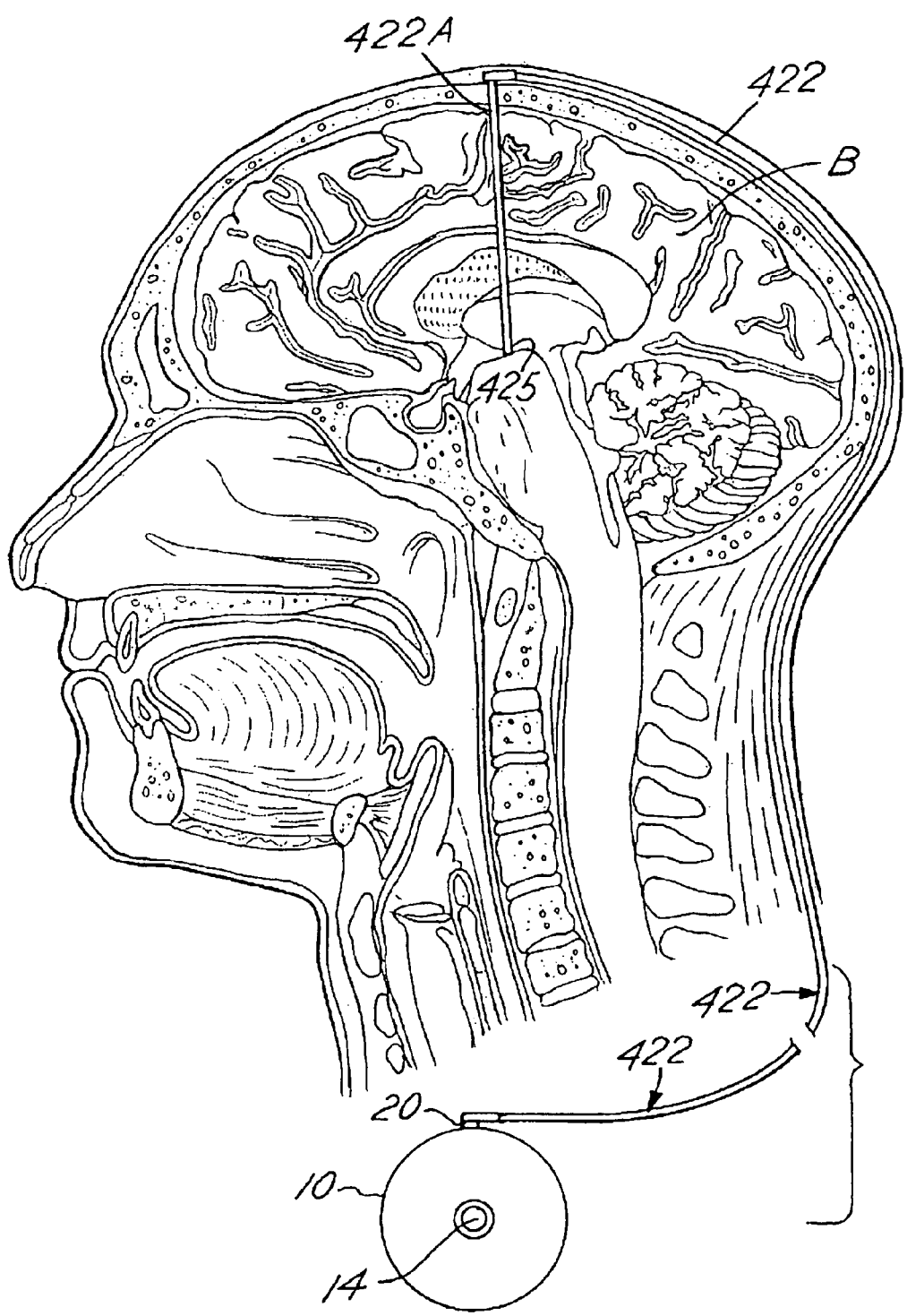
FIGS. 2 and 2A are diagrammatic illustrations of a catheter implanted in a brain according to a preferred embodiment.
Figure 2A:
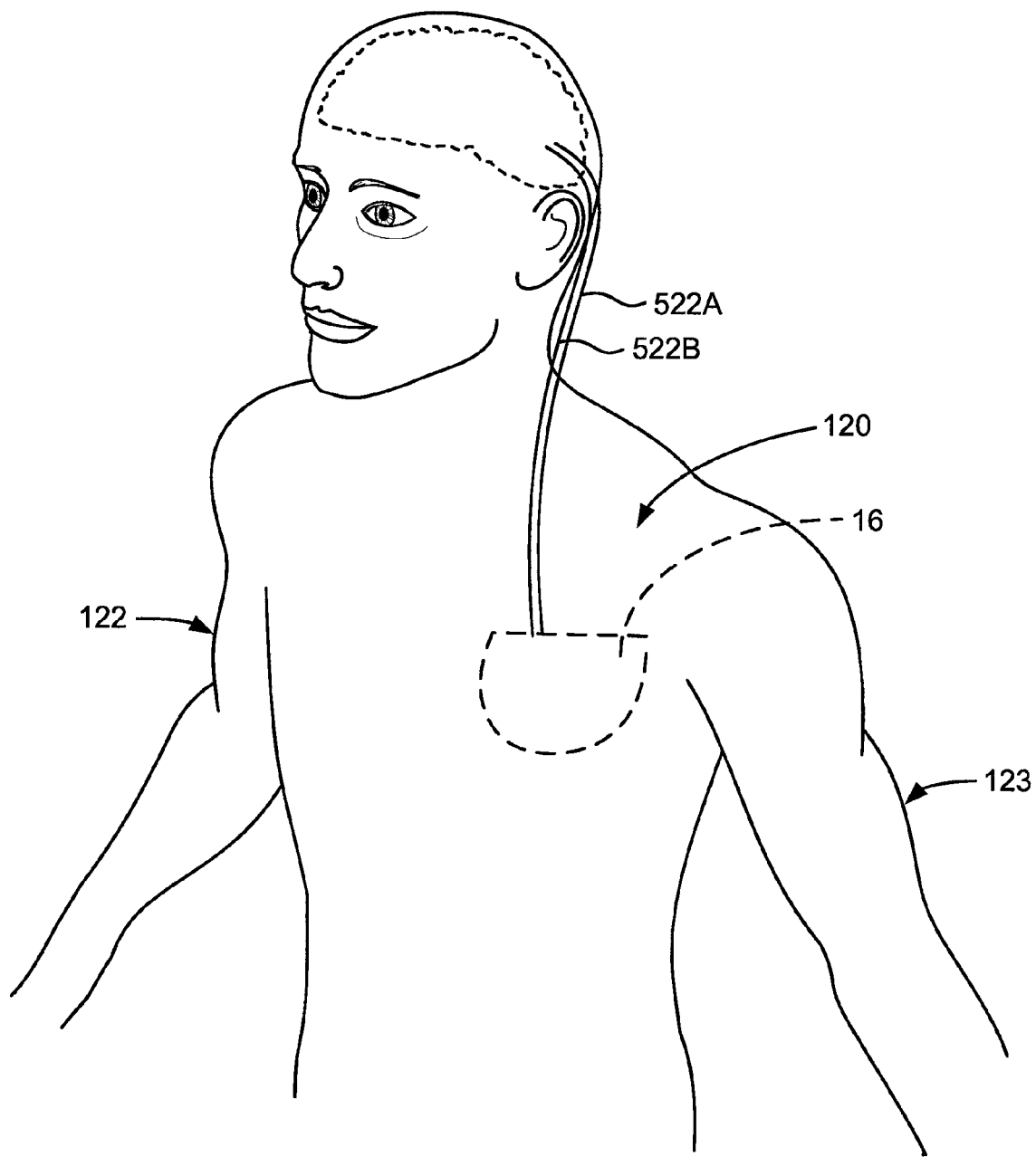

Referring to FIG. 2, in another embodiment, the system or device of the present invention may utilize drug delivery as the form of treatment therapy. A pump 10 may be implanted below the skin of a patient. The pump 10 has a port 14 into which a hypodermic needle can be inserted through the skin to inject a quantity of a liquid agent, such as a medication or drug. The liquid agent is delivered from pump 10 through a catheter port 20 into a catheter 422. Catheter 422 is positioned to deliver the agent to specific infusion sites in a brain (B). Pump 10 may take the form of any number of known implantable pumps including for example that which is disclosed in U.S. Pat. No. 4,692,147.

Like electrical stimulation, drug delivery may be use to influence nerve tissue to increase or decrease its production of neurotrophins. Any number of drugs may be administered including, but not limited to, an anesthetic, a GABA agonist, a GABA antagonist, a glutamate antagonist, a glutamate agonist, a degrading enzyme, a reuptake blocker, and a dopamine antagonist. An activating chemical may be used and includes any chemical that causes an increase in the discharge rate of neurotrophins from a region. An example (for projection neurons which receive glutamatergic excitation and GABA inhibition) would be an agonist of the transmitter substance glutamate (facilitating the excitation) or a GABA antagonist (blocking the inhibition). Conversely, a blocking chemical may be used and includes any chemical that inhibits the projection neurons thereby causing a decrease in the discharge rate of neurotrophins from a region. An example would be a glutamate antagonist (blocks excitatory input to the projection nerve cells) or a GABA agonist (enhances inhibition of the projection neurons) or a local anaesthetic such as lidocaine and related compounds or an infusion of ions (for example Potassium, Calcium, Sodium, Chloride) or agents to alter ionic concentration or pH level. An example of an activating chemical is a GABA antagonist such as bicuculline and an example of a blocking agent would be a GABA agonist such as baclofen.

The distal end of catheter 422 terminates in a cylindrical hollow tube 422A having a distal end 425 implanted, by conventional stereotactic surgical techniques, into a portion of the brain to affect tissue within the human brain. Tube 422A is surgically implanted through a hole in the skull and catheter 422 is implanted between the skull and the scalp as shown in FIG. 2. Catheter 422 is joined to pump 10 in the manner shown. Pump 10 is implanted in a human body in a subcutaneous pocket located in the chest below the clavicle. Alternatively, pump 10 may be implanted in the abdomen.

Catheter 422 may be divided into twin tubes 422A and 422B (not shown) that are implanted into the brain bilaterally. Alternatively, tube 422B (not shown) implanted on the other side of the brain may be supplied with drugs from a separate catheter and pump.

The pump 10 may be programmed to deliver drug according to a particular dosage and/or time interval. For example, the pump may delivery drug therapy over a first period when the dose is higher to increase expression of neurotrophic factors followed by a longer period of ongoing delivery to maintain neurotrophin factor levels and secondary trophic effects like axonal sprouting and synaptogenesis.

Alternatively, a combination of treatment therapies may be delivered to provide influencing of various neuronal types. For example, it may be desirable to concurrently influence, via drug and/or electrical stimulation, the neurons in the hippocampus and other nerve elements in the human body to achieve an improved result. Such a device to utilize both forms of treatment therapy may be that which is disclosed, for example, in U.S. Pat. No. 5,782,798. In addition to affecting the deep brain, it may be desirable to affect concurrently other portions of the human body.

Referring to FIG. 3, the overall components of the implanted device 16 are shown (similar components may also be found for pump 10). The stimulus pulse frequency is controlled by programming a value to a programmable frequency generator 208 using bus 202. The programmable frequency generator provides an interrupt signal to microprocessor 200 through an interrupt line 210 when each stimulus pulse is to be generated. The frequency generator may be implemented by model CDP1878 sold by Harris Corporation. The amplitude for each stimulus pulse is programmed to a digital to analog converter 218 using bus 202. The analog output is conveyed through a conductor 220 to an output driver circuit 224 to control stimulus amplitude.

Microprocessor 200 also programs a pulse width control module 214 using bus 202. The pulse width control provides an enabling pulse of duration equal to the pulse width via a conductor 216. Pulses with the selected characteristics are then delivered from device 16 through cable 522 and lead 522A to the desired regions of the brain.

At the time the stimulation device 16 is implanted, the clinician programs certain key parameters into the memory of the implanted device via telemetry. These parameters may be updated subsequently as needed.

The embodiments of the present invention shown above are open-loop systems. The microcomputer algorithm programmed by the clinician sets the stimulation parameters of signal generator 16. This algorithm may change the parameter values over time but does so independent of any changes in symptoms the patient may be experiencing. Alternatively, a closed-loop system discussed below which incorporate a sensor 130 to provide feedback could be used to provide enhanced results. Sensor 130 can be used with a closed loop feedback system in order to automatically determine the level of electrical stimulation and/or drug delivery necessary to achieve the desired regulation of neurotrophic factors. In a closed-loop embodiment, microprocessor 200 executes a control algorithm in order to provide stimulation with closed loop feedback control. Such an algorithm may analyze a sensed signal and deliver the electrical of chemical treatment therapy based on the sensed signal falling within or outside predetermined values or windows, for example, for BDNF and other neurotrophins (e.g., NGF, CNTF, FGF EGF, NT-3) and corticosteroids.

The control algorithm may be operable on-line or in real time by detecting an electophysiological or chemical signal or off line by measuring a predetermined clinical benefit. Alternatively, the therapy could be guided by the goal of maintaining the population of neurotrophic factors at to a certain level. This could be assessed using the techniques described below.

For example, the sensor 130 may generate a sensor signal related to the level of a particular neurotrophic factor (using known techniques such as microdialysis or brain probe). As another example, the sensor 130 may generate a sensor signal related to the extent of neuronal loss. In an embodiment, the extent of electrical activity or the levels of a neurochemical may be measured that are indicative of neuronal loss. For example magnetic resonance spectroscopy may be used to sense the N-acetylaspartate (NAA) to creatine (Cr) ratio (NAA/Cr) as an indicator of neuronal loss. Alternatively, the neuronal loss may be estimated by measuring the volume of the neural structure of interest, which may be achieved by Magnetic Resonance Imaging vollumetry. Any other techniques may also be used to sense the extent of neuronal loss including, for example, MR volumetry, DWI, magnetization transfer MR imaging, and 1H MRS and PET).

As another example, the sensing may provide an indication of a cognitive or neurological disorder. U.S. Pat. No. 6,227,203 provides examples of various types of sensors that may be used to detect a symptom or a condition of a cognitive disorder and responsively generate a neurological signal. In an embodiment, a neurochemical characteristic of the cognitive function may be sensed, additionally or alternatively. For example, sensing of local levels of neurotransmitters (glutamate, GABA, Aspartate), local pH or ion concentration, lactate levels, local cerebral blood flow, glucose utilization or oxygen extraction may also be used as the input component of a closed loop system. These measurements could be taken at rest or in response to a specific memory or cognitive task or in response to a specific sensory or motor stimulus. In another embodiment, an electro-physiological characteristic of the cognitive function may be sensed, for example, the frequency and pattern of discharge of individual neurons or the amplitude of a local electric field potential. The information contained within the neuronal firing spike train, including spike amplitude, frequency of action potentials, signal to noise ratio, the spatial and temporal features and the pattern of neuronal firing, oscillation behavior and inter-neuronal correlated activity could be used to deliver therapies on a contingency basis in a closed loop system. Moreover, treatment therapy delivered may be immediate or delayed, diurnal, constant or intermittent depending on contingencies as defined by the closed loop system.

In one embodiment, the system may provide continuous closed-loop feedback control. In another embodiment, the system may be switchable between open-loop and closed-loop by operator control.

Referring back to FIG. 3, the system may optionally utilize closed-loop feedback control having an analog to digital converter 206 coupled to sensor 130. Output of the A-to-D converter 206 is connected to microprocessor 200 through peripheral bus 202 including address, data and control lines. Microprocessor 200 processes sensor data in different ways depending on the type of transducer in use and regulates delivery, via a control algorithm, of electrical stimulation and/or drug delivery based on the sensed signal. For example, when the signal on sensor 130 exceeds a level programmed by the clinician and stored in a memory 204, increasing amounts of treatment therapy may be applied through an output driver 224. In the case of electrical stimulation, a parameter of the stimulation may be adjusted such as amplitude, pulse width and/or frequency.

Thus, embodiments of REGULATION OF NEUROTROPHINS are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A method for regulating the level of one or more neurotrophic factors in neural tissue of the cortex or sub-cortex to treat or alleviate a neurological disorder involving neuronal loss or damage, the method comprising:
   (A) sensing a symptom of the neurological disorder within said neural tissue of the cortex or sub-cortex, wherein said sensing detects amounts of said one or more neurotrophic factors; and
   (B) relaying said sensing to a signal generator to deliver electrical stimulation to the tissue of a neural circuit of the limbic system selected from the group consisting of the hippocampus, the fornix, the mammillary body, the anterior thalamic nuclei, and the cingulate gyrus through an electrode to thereby increase or decrease the level of the one or more neurotrophic factors and treat or alleviate the neurological disorder.

2. The method, as claimed in claim 1, wherein (B) comprises selecting amplitude, width and frequency of stimulation by the electrode.

3. The method, as claimed in claim 1, wherein (B) comprises operating the signal generator to pulse at a frequency between 2 Hertz and 1000 Hertz.

4. The method, as claimed in claim 1, wherein (B) comprises operating the signal generator to pulse at a pulse amplitude between 0.1 Volts to 10.0 Volts.

5. The method, as claimed in claim 1, wherein (B) comprises operating the signal generator to pulse at a pulse width between 30 microseconds and 150 microseconds.

6. The method, as claimed in claim 1, wherein (B) comprises operating the signal generator in a monopolar configuration.

7. The method, as claimed in claim 1, wherein (B) comprises operating the signal generator in a bipolar configuration.

8. The method, as claimed in claim 1, wherein (B) comprises operating the signal generator in a multipolar configuration.

9. The method, as claimed in claim 1, wherein (B) comprises operating the signal generator in a continuous mode.

10. The method, as claimed in claim 1, wherein (B) comprises operating the signal generator in a cyclical mode.

11. The method, as claimed in claim 1, wherein (B) comprises selecting between an open loop and a closed loop mode of operation.

12. The method, as claimed in claim 1, wherein (A) comprises generating a sensor signal indicative of the level of the one or more neurotrophic factors and (B) comprises regulating the operation of the signal generator in response to the sensor signal.

13. The method, as claimed in claim 12, wherein (A) comprises detecting the extent of neuronal loss or damage.

14. The method, as claimed in claim 12, wherein (A) comprises detecting the extent of a neurological disorder.

15. The method, as claimed in claim 12, wherein (B) comprises executing a control algorithm.

16. The method, as claimed in claim 12, wherein (B) comprises adjusting at least one parameter of the stimulation, the parameter being selected from the group consisting of amplitude, pulse width and frequency.

17. The method, as claimed in claim 1, further comprising:
   (C) implanting at least one secondary electrode so that a secondary stimulation portion lies in communication with a portion of the body;
   (D) coupling the secondary electrode to the signal generator; and
   (E) operating the signal generator to stimulate the portion of the body.

18. The method, as claimed in claim 1, further comprising:
   (C) implanting at least one catheter so that a discharge portion lies in communication with a second neural tissue of said body;
   (D) coupling the catheter to a pump; and
   (E) operating the pump to deliver drug to the second neural tissue to thereby alter the level of a neurotrophin generated by the second neural tissue.

19. A therapeutic treatment method for regulating the level of one or more neurotrophic factors in neural tissue of the cortex or sub-cortex to treat or alleviate a neurological disorder involving neuronal loss or damage, the method comprising:

(A) sensing a symptom of the neurological disorder within said tissue of a neural circuit of the limbic system selected from the group consisting of the hippocampus, the fornix, the mammillary body, the anterior thalamic nuclei, and the cingulated gyrus, wherein said sensing detects amounts of said one or more neurotrophic factors; and (B) relaying said sensing to a pump to deliver at least one drug to the neural tissue of the cortex or sub-cortex through a catheter to thereby increase or decrease the level of the one or more neurotrophic factors and treat or alleviate the neurological disorder.

20. The method, as claimed in claim 19, wherein (B) comprises selecting a time interval for drug delivery.

21. The method, as claimed in claim 19, wherein (B) comprises selecting a drug dosage.

22. The method, as claimed in claim 19, wherein (A) comprises generating a sensor signal indicative of the level of the one or more neurotrophic factors and (B) comprises regulating the operation of the pump in response to the sensor.

23. The method, as claimed in claim 22, wherein (A) comprises detecting the extent of neuronal loss or damage.

24. The method, as claimed in claim 22, wherein (A) comprises detecting the extent of a neurological disorder.

25. The method, as claimed in claim 22, wherein (A) comprises executing a control algorithm.

26. The method, as claimed in claim 19, further comprising:

(C) implanting at least one electrode so that a stimulation portion lies in communication with a second neural tissue;

(D) coupling the electrode to a signal generator; and (E) operating the signal generator to stimulate the second neural tissue.

27. The method, as claimed in claim 19, further comprising:

(C) implanting at least one secondary catheter so that a second discharge portion lies in communication with a second portion of the neural tissue;

(D) coupling the secondary catheter to a pump; and (E) operating the pump to deliver drug to the second portion of the neural tissue.

28. A method for regulating the level of one or more neurotrophic factors in neural tissue of the cortex or sub-cortex to treat or alleviate a neurological disorder involving neuronal loss or damage, the method comprising:

(A) sensing a symptom of the neurological disorder within said tissue of the cortex or sub-cortex, wherein said sensing detects amounts of neurotrophic factors;

(B) relaying said sensing to a signal generator to deliver electrical stimulation to the tissue of a neural circuit of the limbic system selected from the group consisting of the hippocampus, the fornix, the mammillary body, the anterior thalamic nuclei, and the cingulated gyrus through an electrode to thereby increase or decrease the level of the one or more neurotrophic factors; and (C) relaying said sensing to a pump to discharge a predetermined dosage of at least one drug through a catheter into the neural tissue of the cortex or the sub-cortex to thereby further increase or decrease the level of the one or more neurotrophic factors and treat or alleviate the neurological disorder.

(d) Inventor Lozano did not sign the oath/declaration filed on Nov. 14, 2009, Therefore, a substitute Oath/Declaration is required to remedy this deficiency. See MPEP 602.03.

e) Corrected drawings for FIG. 2A are required, as reproducibility may be an issue with the respective drawings submitted Jan. 14, 2009. See MPEP 608.02(V)(I).

* * * * *